(12) United States Patent
Kim (10) Patent No.: US 10,606,053 B2
(45) Date of Patent: Mar. 31, 2020

(54) TESTING DEVICE, FOR BODY FLUID ANALYSIS, USING NATURAL LIGHT

(71) Applicant: JONGROMEDICAL CO., LTD., Daegu (KR)

(72) Inventor: Ji Hoon Kim, Daegu (KR)

(73) Assignee: JONGROMEDICAL CO., LTD., Daegu (KR)

( * ) Notice: Subject to any disclaimer, the term of this patent is extended or adjusted under 35 U.S.C. 154(b) by 0 days.

(21) Appl. No.: 16/062,632

(22) PCT Filed: Nov. 22, 2016

(86) PCT No.: PCT/KR2016/013460
§ 371 (c)(1),
(2) Date: Jun. 15, 2018

(87) PCT Pub. No.: WO2017/104991
PCT Pub. Date: Jun. 22, 2017

(65) Prior Publication Data
US 2019/0120750 A1 Apr. 25, 2019

(30) Foreign Application Priority Data
Dec. 15, 2015 (KR) .......................... 10-2015-0179433

(51) Int. Cl.
*G01N 21/31* (2006.01)
*G02B 21/00* (2006.01)
(Continued)

(52) U.S. Cl.
CPC ...... *G02B 21/0008* (2013.01); *A61B 10/0012* (2013.01); *G01N 21/255* (2013.01);
(Continued)

(58) Field of Classification Search
CPC .............. G02B 21/0008; G02B 21/248; G01N 33/487; G01N 21/255; A61B 10/00; A61B 10/0012
See application file for complete search history.

(56) References Cited

U.S. PATENT DOCUMENTS 5,062,697 A * 11/1991 Mitchell ............ G02B 21/0008
359/379
5,572,370 A * 11/1996 Cho ........................ G02B 25/02
359/379

(Continued)

FOREIGN PATENT DOCUMENTS

KR 10-2008-0056034 A 6/2008
KR 10-2011-0019165 A 2/2011
(Continued)

OTHER PUBLICATIONS

International Search Report for PCT/KR2016/013460 dated Feb. 16, 2017 from Korean Intellectual Property Office.

*Primary Examiner* — Maurice C Smith
(74) *Attorney, Agent, or Firm* — Revolution IP, PLLC (57) ABSTRACT

A testing device for body fluid analysis includes: a sheet unit having a sheet of which a first surface receives body fluid of a user to be deposited thereon; a contact unit having a magnifying lens group for magnifying the body fluid deposited on the sheet, the contact unit being provided with a first side at which the magnifying lens group is placed to face the first surface of the sheet and being provided with a second side at which a guide adhering to a photographing means obtaining an image of the body fluid magnified by the magnifying lens group or coming into contact with around an eye of the user is placed; and a light source unit placed to face a second surface of the sheet of the sheet unit in a direction facing the contact unit with the sheet unit in between.

8 Claims, 7 Drawing Sheets

(51) Int. Cl.
    *A61B 10/00*     (2006.01)
    *G02B 15/10*     (2006.01)
    *G01N 21/25*     (2006.01)
    *G01N 33/487*     (2006.01)
    *G02B 21/06*     (2006.01)
    *G02B 21/26*     (2006.01)

(52) U.S. Cl.
    CPC ........... G01N 21/31 (2013.01); G01N 33/487 (2013.01); G02B 15/10 (2013.01); G02B 21/06 (2013.01); G02B 21/26 (2013.01); *G01N 2201/063* (2013.01)

(56) References Cited

U.S. PATENT DOCUMENTS

| | | | |
|---|---|---|---|
| 10,070,847 B2 * | 9/2018 | Hung | A61B 10/0012 |
| 2002/0080240 A1 * | 6/2002 | Omi | G02B 21/365 |
| | | | 348/207.99 |
| 2003/0179446 A1 * | 9/2003 | Yeh | A61B 10/0012 |
| | | | 359/368 |
| 2004/0066140 A1 * | 4/2004 | Omoto | H05B 33/145 |
| | | | 313/512 |
| 2008/0147053 A1 | 6/2008 | Kang et al. | |
| 2011/0282247 A1 * | 11/2011 | Denise | A61B 5/0059 |
| | | | 600/588 |
| 2014/0168405 A1 * | 6/2014 | Chung Wo | G02B 21/34 |
| | | | 348/80 |
| 2014/0184779 A1 * | 7/2014 | Siano | G02B 21/0008 |
| | | | 348/80 |
| 2016/0282593 A1 * | 9/2016 | Yan | G02B 21/0008 |
| 2017/0138840 A1 * | 5/2017 | Lin | C12M 41/12 |
| 2017/0160534 A1 * | 6/2017 | Fan | G02B 21/362 |
| 2017/0329116 A1 * | 11/2017 | Hsu | G02B 21/0008 |
| 2017/0329120 A1 * | 11/2017 | Hsu | G02B 21/362 |
| 2017/0330321 A1 * | 11/2017 | Hsu | G06T 7/0012 |

FOREIGN PATENT DOCUMENTS

| | | |
|---|---|---|
| KR | 10-2013-0130443 A | 12/2013 |
| KR | 10-2014-0132260 A | 11/2014 |
| KR | 10-1533107 B1 | 7/2015 |

* cited by examiner

[FIG. 7] (a) Infertile period (b) Transition period (c) Fertile period

TESTING DEVICE, FOR BODY FLUID ANALYSIS, USING NATURAL LIGHT

TECHNICAL FIELD

The present invention relates to a testing device for body fluid analysis using natural light. More particularly, the present invention relates to a testing device for body fluid analysis, the device serving as a tester which is portable and easy to use, whereby a user is able to quickly conduct self-testing any time using body fluid of the user and to identify the analysis result.

BACKGROUND ART

Generally, people should visit a specialized medical institution to check there health state and body state. However, in order to receive diagnosis, people need to set aside time for visiting a specialized medical institution during busy work time, and it takes much time and money to perform the complicated procedure. Thus, most people ignore endurable discomfort, and visit specialized medical institutions only when having unendurable pain or discomfort.

In order to solve the inconvenience, techniques have been developed wherein various types of advanced equipment are used to frequently check one's body state and the result is transmitted to a specialized medical institution via a network. However, techniques that are commercialized and are actually used in practice are extremely rare.

Preferably, the use of a simple tester, which has been used for a long time, continues and is increasingly used by the younger generation due to ease of use, low cost, and convenience, and thus visiting a specialized medical institution is unnecessary.

Such a tester detects biochemical substances such as hormones discharged under particular circumstances by using secretions from people's bodies, e.g., saliva, urine, sweat, etc. The tester is relatively highly accurate and easy to use. Accordingly, as a commonly used testing means, testers for pregnancy testing, diabetes diagnosis, and blood sugar checking are used.

Recently, due to increase in the age at marriage, stress, etc., the number of couples who are infertile and have difficulty in becoming pregnant has increased, and thus the use of pregnancy tester has greatly increased. However, the pregnancy tester may determine only pregnancy or not and is not helpful for the user who is infertile and has difficulty in becoming pregnant. Furthermore, only the woman's pregnancy is identified, and the woman's pregnancy probability, the man's fertilization ability, etc. are identified only by a medical institution's consultation.

DISCLOSURE

Technical Problem

Accordingly, the present invention is intended to propose a testing device for body fluid analysis, the device serving as a tester which is portable and easy to use, whereby a user is able to quickly conduct self-testing any time using body fluid of the user and to identify the analysis result.

Also, the present invention is intended to propose a testing device for body fluid analysis, the device being available for both women and men, whereby a woman may identify the period of high pregnancy probability by checking her ovulation period and a man may identify his sperm viability, thereby increasing pregnancy probability.

Technical Solution

In order to accomplish the above object, according to the present invention, there is provided a testing device for body fluid analysis, the device including: a sheet unit having a sheet of which a first surface receives body fluid of a user to be deposited thereon; a contact unit having a magnifying lens group for magnifying the body fluid deposited on the sheet, the contact unit being provided with a first side at which the magnifying lens group is placed to face the first surface of the sheet and being provided with a second side at which a guide adhering to a photographing means obtaining an image of the body fluid magnified by the magnifying lens group is placed; and a light source unit placed to face a second surface of the sheet of the sheet unit in a direction facing the contact unit with the sheet unit in between, the light source unit supplying external light to the second surface of the sheet.

The light source unit may be formed in a shape of a hollow pipe.

The light source unit may be formed with a body hole as a light entering hole through which light enters.

The light source unit may include a light transmissive film between a light entering hole through which light enters and the sheet unit.

The film may transmit only a predetermined wavelength of the external light such that the external light appears in a particular color.

The sheet unit may be provided with mounting portions respectively formed on a side of the first surface and a side of the second surface, and the contact unit and the light source unit with the sheet unit in between may be respectively coupled to the mounting portions formed on the sides of the first and second surfaces of the sheet unit.

The contact unit and the light source unit may be formed in an integrated manner, and the sheet unit may be fitted between the contact unit and the light source unit in such a manner as to be inserted and discharged.

The contact unit and the light source unit may be formed with a hole or a slit in between for insertion of the sheet unit.

The sheet may be formed of any one material of light transmissive synthetic resin, natural rubber, and glass.

The sheet may be formed of a light transmissive material, the sheet being colored in a particular color or being formed of a material transmitting a particular light wavelength.

Advantageous Effects

According to the present invention, the testing device for the body fluid analysis serves as a tester which is portable and easy to use, whereby the user is able to quickly conduct self-testing any time using the body fluid of the user and to identify the analysis result.

According to the present invention, the testing device for the body fluid analysis is available for both women and men, whereby a woman may identify the period of high pregnancy probability by checking her ovulation period and a man may identify his sperm viability, thereby increasing pregnancy probability.

BEST MODE

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear. In the drawing, certain features presented in the drawings are expanded, reduced, or simplified for easy explanation, and the drawings and the constituent elements may not be appropriately illustrated. However, those of ordinary skill in the art could easily understand such detailed matters.

Figure 1:
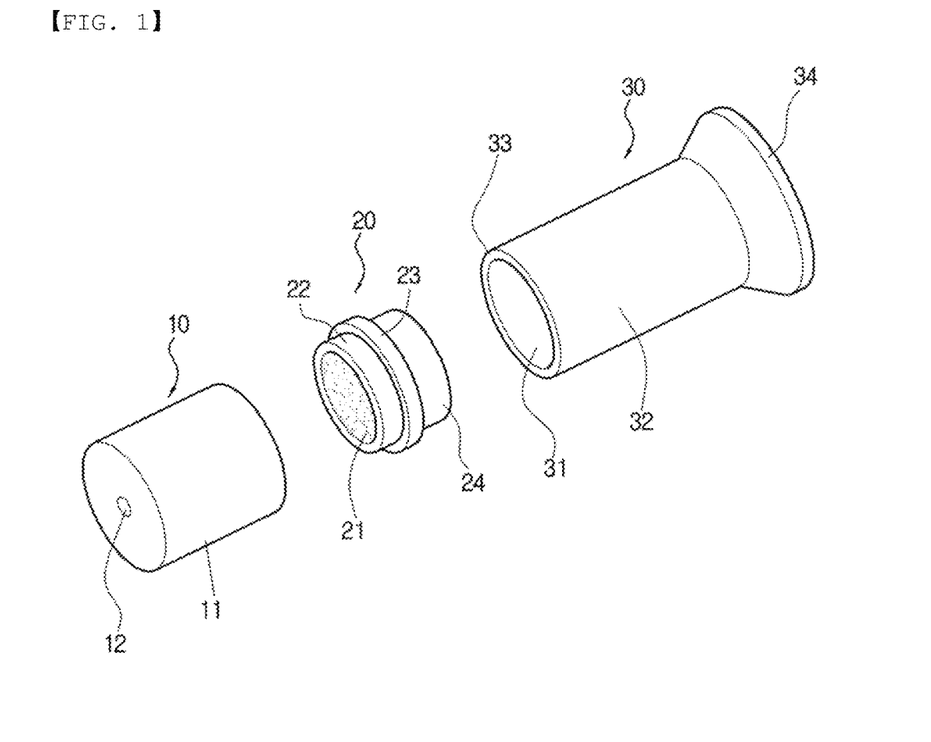
FIG. 1 is an exploded perspective diagram illustrating a testing device for body fluid analysis according to a first exemplary embodiment of the present invention.
Figure 2:
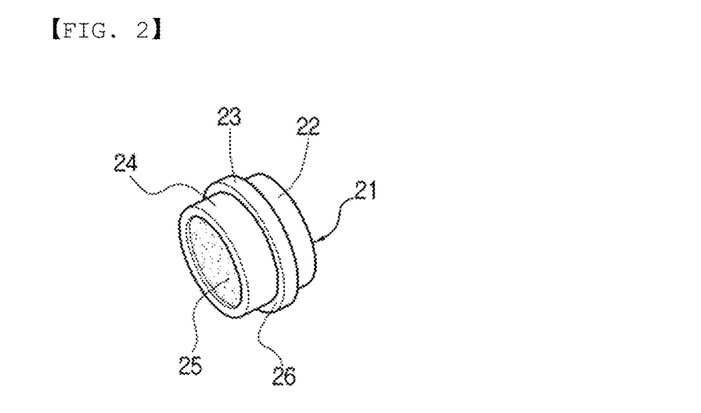
FIG. 2 is a perspective diagram illustrating the opposite surface of a base in FIG. 1.
Figure 3:
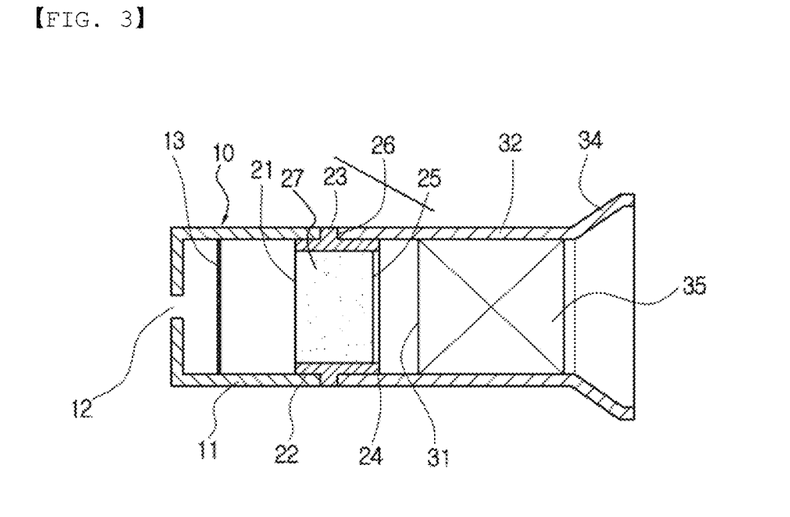
FIG. 3 is a cross-sectional diagram illustrating an example of a testing device for body fluid analysis.

FIGS. 1 to 3 are diagrams illustrating an example of a testing device for body fluid analysis according to a first exemplary embodiment of the present invention. FIG. 1 is an exploded perspective diagram illustrating a testing device for body fluid analysis according to a first exemplary embodiment of the present invention. FIG. 2 is a perspective diagram illustrating the opposite surface of a base in FIG. 1. FIG. 3 is a cross-sectional diagram illustrating an example of a testing device for body fluid analysis.

Referring to FIGS. 1 to 3, according to the present invention, the testing device for the body fluid analysis includes: a sheet unit 20 having a sheet of which a first surface receives body fluid of the user to be deposited thereon; a contact unit 30 having a magnifying lens group for magnifying the body fluid deposited on the sheet 27 of the sheet unit 20, the contact unit being provided with a first side at which the magnifying lens group is placed to face the first surface 25 of the sheet 27 and being provided a second side at which a guide 34 adhering to a photographing means obtaining an image of the body fluid magnified by the magnifying lens group is placed; and a light source unit 10 placed to face the first surface of the sheet unit 20 in a direction facing the contact unit 30 with the sheet unit 20 in between, the light source unit providing external light to the first surface.

The light source unit 10 provides external light to the sheet unit 20 so as to serve as a light source enabling an image of the body fluid deposited in the sheet unit 20 to be obtained. The light source unit 10 includes a body 11 formed in a hollow cylindrical shape in such a manner as to provide light to a bottom surface of the sheet 27, which is a second surface of the sheet unit 20. An end of the light source unit 10 is coupled to the sheet unit 20 by being fitted on a mounting portion 22 formed around the side of a second surface 21 of the sheet of the sheet unit 20. A surface opposite to the end is provided with a body hole 12 as shown in FIG. 1. The body hole 12 applies scattering and diffraction of external light to make the image of the body fluid deposited on the sheet unit 20 clear. The body hole 12 is not necessarily formed, and the shape, number, and position of the body hole 12 may differ.

Particularly, the light source unit 10 may include a film 13 placed between the body hole 12 and the sheet unit 20 as shown in FIG. 3. That is, the film 13 may be provided in a direction in which light enters on the basis of the sheet unit 20. The film 13 may be formed in various thicknesses by using various materials, such as a transmittance thin film, a transmittance plate, and glass, and the present invention is not limited to the materials of the film 13. Hereinafter, the term "film" includes members of the above-described material or form. The film 13 changes natural light, which is close to white light, to a particular color. That is, the film 13 is a means for filtering out a particular wavelength from white light so as to only transmit light of a predetermined wavelength, or the film 13 is colored in a particular color to make white light to be colored. Accordingly, the film 13 allows monochromatic light to be transmitted to the sheet unit 20 such that the crystal of the body fluid deposited on the sheet unit 20 is more clearly distinguished, and the crystal is easily distinguished from the background in image processing. Here, when the sheet of the sheet unit 20 has a material and feature similar to the film 13 so as to serve as the film 13, the film 13 may be omitted.

The sheet unit 20 serves as a stage, and includes the sheet 27 of which a surface 25 receives the body fluid of the user to be deposited thereon. The sheet unit 20 includes: the sheet 27 on which the body fluid is deposited; and a base 23 fixing the sheet 27, blocking external light, and enabling the sheet unit 20 to be coupled to the contact unit 30 and the light source unit 10. Specifically, the sheet 27 is formed of a light transmissive material, such as circular plate glass or synthetic resin. The base 23 is formed in the form of a pipe surrounding the outer circumferential surface of the sheet 27. Mounting portions 22 and 26 are formed on the outer circumferential surface of the base 23. The mounting portions 22 and 26 are formed on a side of the first surface 21 of the sheet 27 and on a side of the second surface 25, respectively. The light source unit 10 is coupled to a first mounting portion 22 formed on the side of the first surface 21, and the contact unit 30 is coupled to a second mounting portion 26 formed on the side of the second surface 25. The base 23 formed on the second surface 25 protrudes from the second surface 25 such that a sheet guard 24 is defined. The sheet guard 24 prevents overflow of the body fluid when depositing the body fluid on the sheet 27, or prevents the body fluid from being put on the inner wall of the contact unit 30, and determines the amount of the body fluid to be deposited.

As described above, the sheet 27 is formed of a light transmissive material, and serves as a stage on which the body fluid is deposited for observation. The user deposits the body fluid on the sheet 27 and dries the body fluid for observation or observes the body fluid in the liquid state. A cover may be configured as needed, but the cover is omitted in the description of the present invention. The sheet 27 is formed of a light transmissive material, and transmits light received on the first surface 21 from the light source unit 10 to the second surface 25 so as to provide background light for the body fluid deposited on the sheet 25. The sheet 27 may diffuse external light such that uniform light may be provided to the second surface 25 of the sheet. To this end, the sheet may be formed of a transparent material, such as a synthetic resin, e.g. acrylic, polyethylene resin, and polycarbonate resin, glass, e.g. soda-lime glass, but the present invention is not limited thereto.

In the meantime, the sheet 27 may be colored or allows only light of a particular wavelength to pass through like the film 13, which has been described in the description of the film 13 in detail, and thus the description thereof will be omitted. The sheet 27 and the base 23 may be formed of the same material in an integrated manner, but in this case, external light may enter through the base 23 and scattered light may be generated, which may interfere with observation of the body fluid. This problem may be solved by coloring the outer circumferential surface of the base 23.

The contact unit 30 couples the sheet unit 20 and a testing terminal such that the testing terminal (not shown) may obtain the image of the body fluid deposited on the sheet unit 20. To this end, the contact unit 30 is coupled to the sheet unit 20 in such a manner that an objective part 31 faces the second surface 25 of the sheet 27. The contact unit 30 is formed in the shape of a hollow pipe, and includes the magnifying lens group 35 therein for magnifying the image of the sheet unit 20. Particularly, by adjusting the length of a stage body 32 of the contact unit 30, the position of the magnifying lens group 35 differs such that magnification and focus are adjusted.

Accordingly, when the testing terminal at different magnification is coupled or when the image of the body fluid is checked by the naked-eye of the user, focus and magnification are adjusted.

In the meantime, the guide 34 is formed at the second side of the contact unit 30. The guide 34 ensures that the magnifying lens group 35 is not in direct contact with the testing terminal, and that a predetermined distance between the testing terminal and the magnifying lens group 35 is maintained for accurate magnification control. Also, the guide 34 prevents light leakage caused by external light such that accurate image of the body fluid is obtained by the testing terminal or the user.

Figure 4:
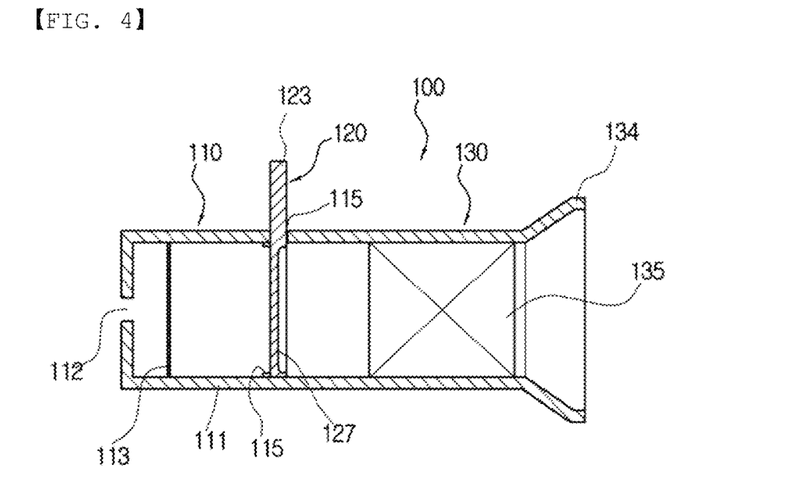
FIG. 4 is a cross-sectional diagram illustrating an example of a testing device for body fluid analysis according to a second exemplary embodiment of the present invention.
Figure 5:
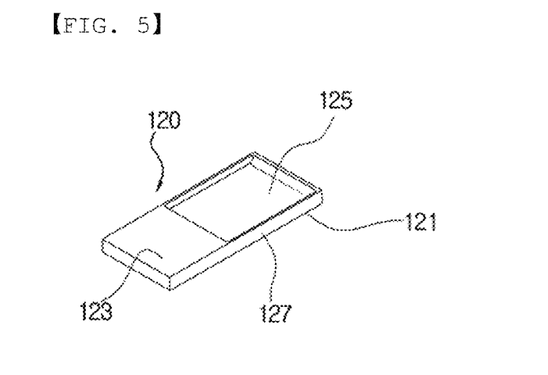
FIG. 5 is a perspective diagram illustrating an example of a sheet of FIG. 4 in detail.

FIG. 4 is a cross-sectional diagram illustrating an example of a testing device for body fluid analysis according to a second exemplary embodiment of the present invention. FIG. 5 is a perspective diagram illustrating an example of a sheet of FIG. 4 in detail.

In the second exemplary embodiment of the present invention, the detailed description of the same or similar features to those of the first exemplary embodiment will be omitted, and the description will be focused on the difference.

Referring to FIGS. 4 and 5, according to the second exemplary embodiment of the present invention, in the testing device for the body fluid analysis, a light source unit 110 and a contact unit 130 are formed in an integrated manner, and a sheet unit 120 is inserted and discharged through a slit 115 provided between the light source unit 110 and the contact unit 130.

Features of the second exemplary embodiment of the present invention are similar to those of the first exemplary embodiment except that the light source unit 110 is directly coupled to the contact unit 130 and the slit 115 is formed, and thus the detailed description thereof will be omitted.

The slit 115 is formed between the light source unit 110 and the contact unit 130, and is formed in size corresponding to the thickness of the sheet unit 130. Also, in a body 111 in which the slit 115 is formed, there is formed a rail guide 115 fixing and supporting the sheet unit 120 inserted through the slit 115, and guiding the insertion of the sheet unit 120. The rail guide 115 may be formed in a manner that does not interfere with transmission of light to the sheet unit 120, and may be formed in any structure that facilitates insertion and discharge of the sheet unit 130. In the meantime, only one slit 115 is formed on a side in the body 111, but another slit 115 may be formed on the opposite side to firm the fixed state and enable the sheet unit 120 to be inserted to the accurate position. That is, the sheet unit 120 may be inserted against a pair of slits 115 into the body 111, but the present invention is not limited thereto.

In the meantime, the sheet unit 120 may be formed in a plate shape, and may be coupled to the testing device by being inserted through the slit 115. The sheet unit 120 includes a base 123 and a sheet 127 that may be formed in an integrated manner, and the base 123 may be colored to block the entrance of external light. Also, the sheet 127 may be formed in a concave manner such that the body fluid of the user may be put in the concave portion.

Figure 6:
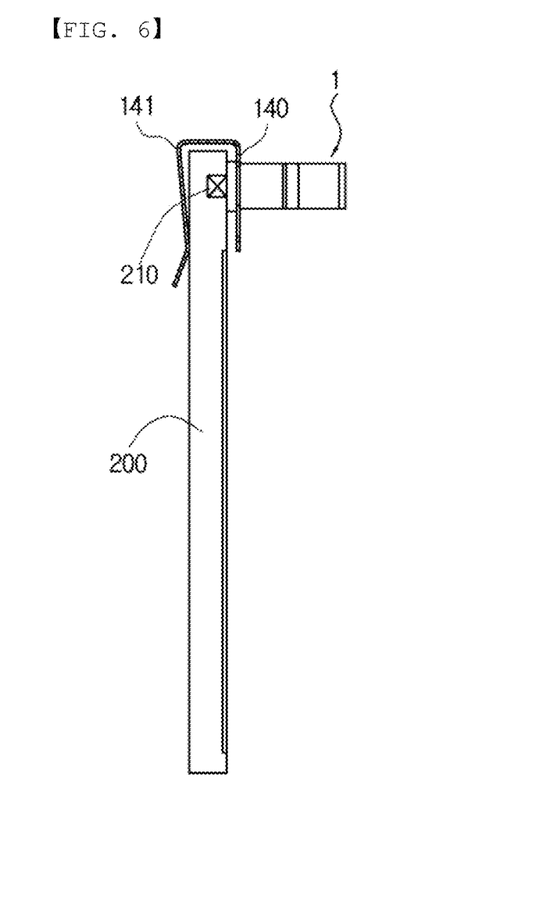
FIG. 6 is a diagram illustrating an example of using a testing device of the present invention.

FIG. 6 is a diagram illustrating an example of using a testing device of the present invention.

Referring to FIG. 6, the testing device for the body fluid analysis of the present invention may include a testing terminal 200, and the testing device 1 and 100 may be used in combination with the testing terminal 200.

According to the present invention, the user of the testing device 1 and 100 may identify the image of the body fluid by directly contacting the user's eye to the guide 34 and 134 of the contact unit 30 and 130, and may recognize the user's state, or the state may be analyzed by the testing terminal 200 as follows.

The testing terminal 200 may be any type of terminal such as a mobile terminal, e.g. a smart phone, a tablet, and a laptop, and a computer terminal capable of photographing and of outputting, transmitting, or analyzing the obtained image. FIG. 6 shows an example that a terminal, such as a smart phone and a tablet, is used, but the present invention is not limited thereto.

The testing terminal 200 and the testing device 1 and 100 may be coupled to each other by a coupling means 140 as shown in FIG. 6. As an example, FIG. 6 shows a coupling means 140 in the form of a clip.

The coupling means 140 couples the testing device 1 and 100 with the testing terminal 200, particularly, in such a manner that the contact unit 30 and 130 corresponds to a camera 210 of the testing terminal 140. To this end, the testing terminal 140 may be coupled to the testing device 1 and 100 in various methods such as the form of a clip, a band, and adsorption. For example, the coupling means 140 in the form of a clip is formed with multiple bent portions 141 such that the testing device 1 and 100 is coupled to the testing terminal 140 by elasticity applied by the bent portions 141. The coupling means 140 may be formed of metal, synthetic resin, or wood with excellent mechanical strength and elasticity, but the present invention is not limited thereto.

Figure 7:
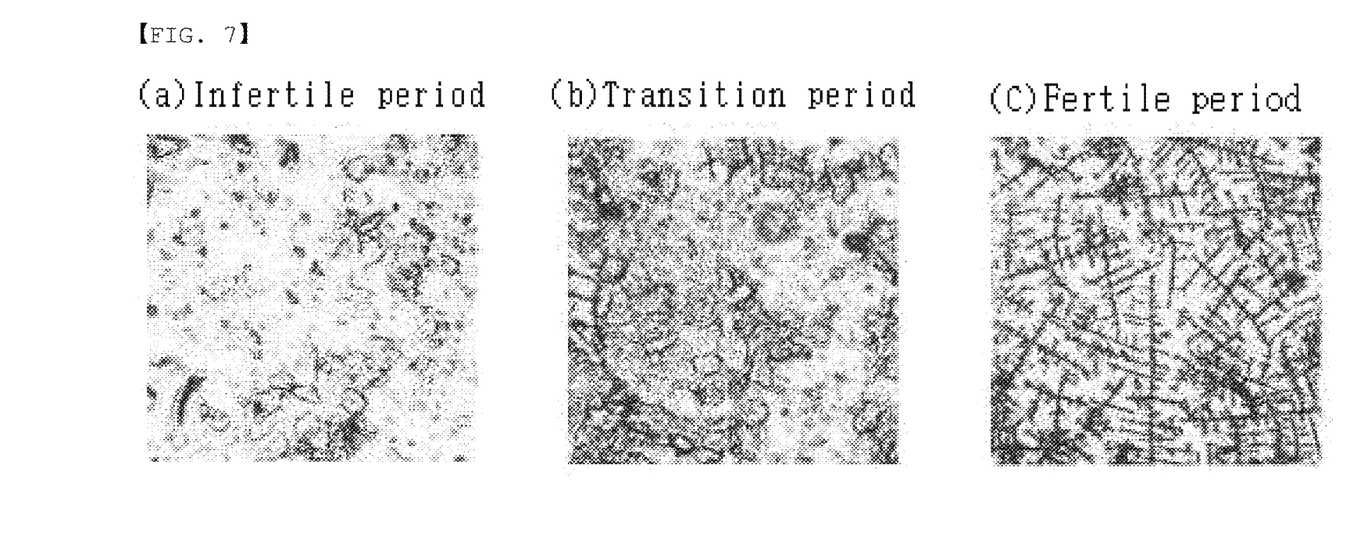
FIG. 7 is a diagram illustrating an example of change in body fluid for a pattern analysis.
Figure 8:
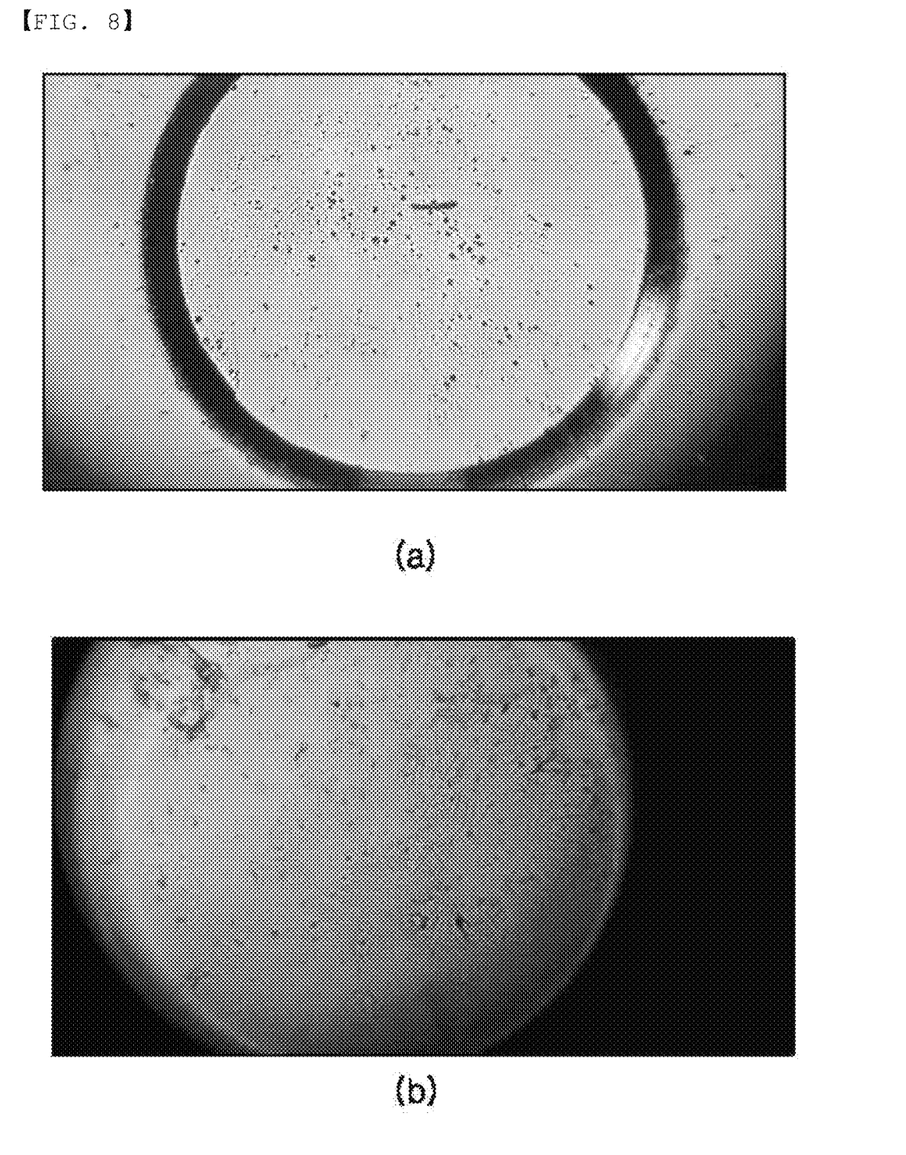
FIG. 8 is a diagram illustrating an example of a test image in which actual body fluid is used.
Figure 9:
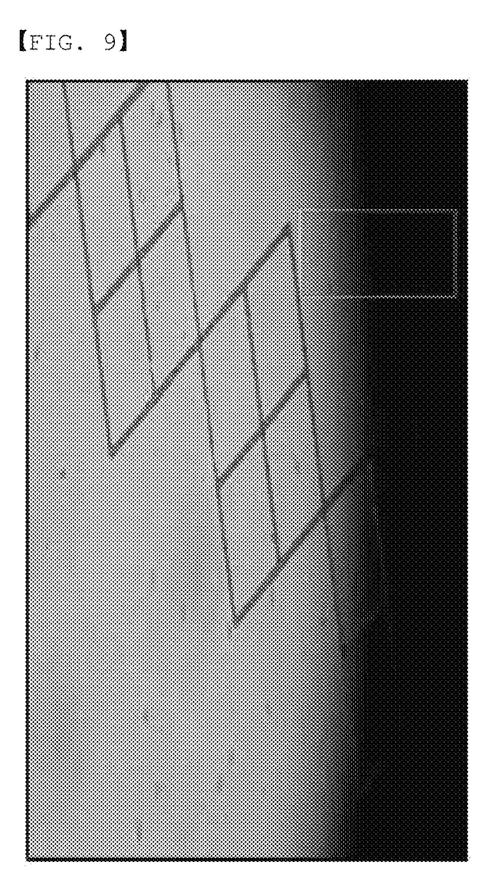
FIG. 9 is a diagram illustrating an example of a subdivision pattern used in analyzing a test image.

FIGS. 7 to 9 are diagrams illustrating an example of a pattern analysis method according to the present invention. FIG. 7 is a diagram illustrating an example of a change in body fluid for a pattern analysis. FIG. 8 is a diagram illustrating an example of a test image in which actual body fluid is used. Also, FIG. 9 is a diagram illustrating an example of a subdivision pattern used in analyzing a test image.

Referring to FIGS. 7 to 9, the body fluid, particularly, the saliva may be used as an indicator of various conditions. The saliva of a woman in the fertile period shows a special sign distinctly. Specifically, due to the influence of estrogen which is a female hormone contained in the saliva of a woman, ovulation may be accurately predicted, and thus married couples suffering from infertility may increase pregnancy probability.

Specifically, when a woman in the fertile period, as the ovulation date gets closer, the secretion rate of the estrogen increases, and also, the salt concentration of the saliva increases. Accordingly, when the saliva is dried for a particular time, different crystal structures of the dried saliva shows depending on the infertile period, the transition period, and the fertile period.

For example, when drying and photographing the saliva of the woman in the infertile period during which ovulation does not occur, an image in which no distinct crystal structure is found is obtained as shown in FIG. 7(a).

FIG. 8 shows the actually obtained image. As shown in FIGS. 7(a) and 8(a), in the infertile period, no specific crystal structure is found, and only some salivary cells are identified.

In the transition period during which the infertile period transitions to the fertile period in which ovulation occurs, the saliva of the woman is slightly crystallized in the form as shown in FIG. 7(b). At this time, the form of the crystals is the form of salivary cells in circular and oblong shapes formed by electrolyte, mucus, enzyme, etc.

Last, in the fertile period during which ovulation occurs, the form in which the crystal extends in one direction, namely, a fern pattern clearly visible as shown in FIG. 7(c). FIG. 8(b) shows an image of actual saliva of the woman in the fertile period. As seen from this, the pattern distinctly distinguished from FIG. 8(a) is identified.

In the body fluid state diagnostic system of the present invention, the state of the saliva is analyzed to identify whether the user is in the fertile period, and the identified information is provided to the user as the analysis information.

That is, the testing terminal 1 and 100 performs image processing on the obtained test image to clarify the crystal line, and determines whether the crystal line is in the form of a closed curve line or in the form of the straight lines in the fern pattern as shown in (c). Particularly, the length and density of the linear pattern is identified. Consequently, the infertile period, the transition period, and the fertile period are determined and the result is provided to the user as the analysis information. Here, the image processing and the determining of the infertile period, the transition period, and the fertile period are possibly adjusted depending on the density and form of the pattern, and thus the detailed description thereof will be omitted.

Also, in image processing, the image is reprocessed in black and white, and the contrast of black and white is distinguished to determine the form of the line, whereby the length and the density is determined. Since various methods may be used, the detailed description thereof will be omitted.

In the meantime, in order to enhance accuracy of image processing and the determination, a subdivision pattern may be used as shown in FIG. 9. That is, how many straight lines or oval lines are present in the region (the region inside the closed line) defined by the pattern is identified, and the analysis information is generated.

Particularly, the subdivision pattern may be provided in a printed form on the magnifying lens group 35 and 135 of the testing device 1 and 100 or on the sheet unit 27 and 127 of the base 20 and 120, or a part of the analysis image may be partitioned in the subdivision pattern by the testing terminal 200 for image processing, but the present invention is not limited thereto.

Figure 10:
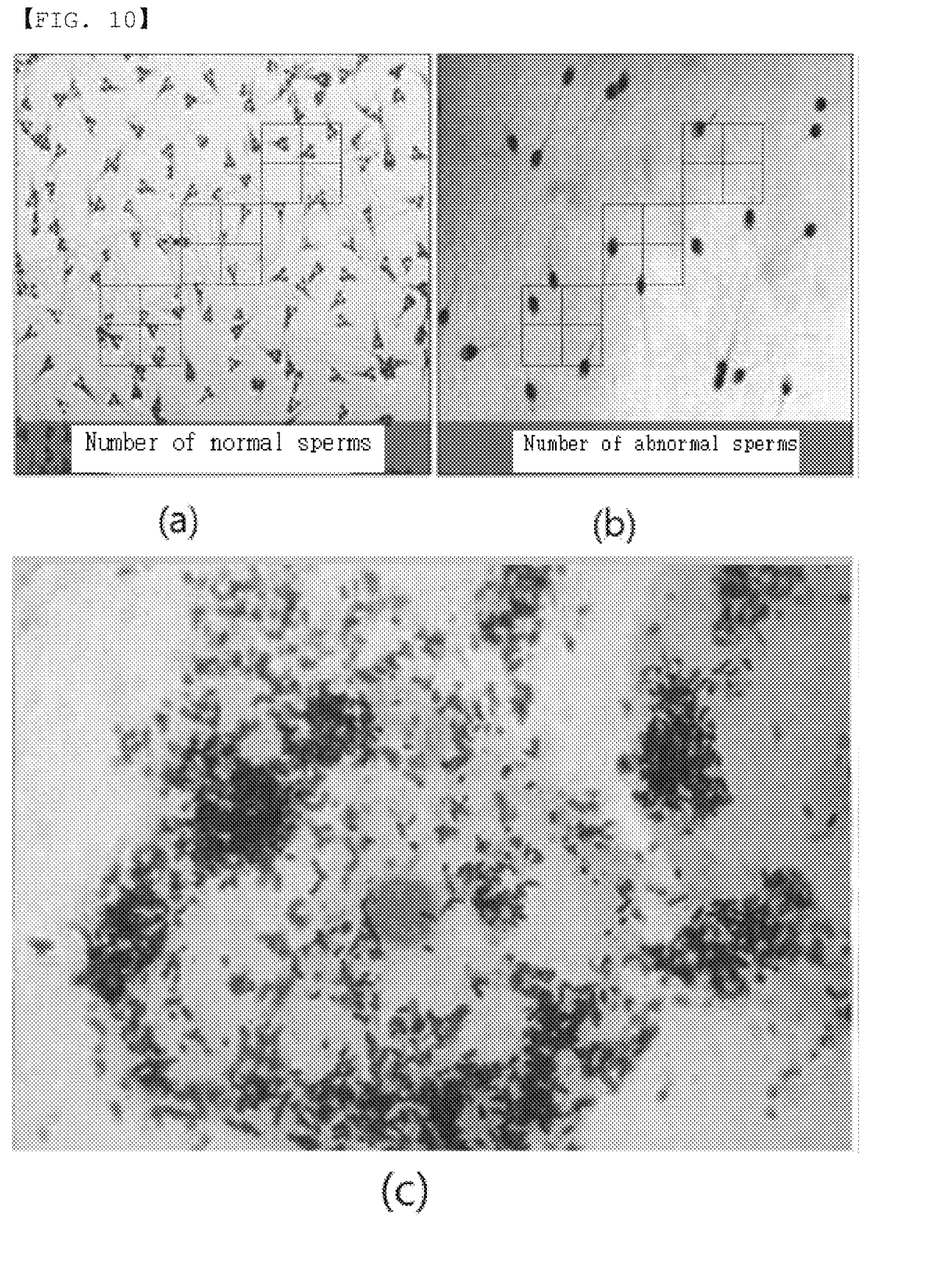
FIG. 10 is a diagram illustrating an example of a case when body fluid is semen.

In the meantime, FIG. 10 is a diagram illustrating an example of a case when body fluid is semen and vaginal discharge.

The analysis information may be generated with respect to semen of a man. When using the state diagnostic system of the present invention with respect to semen of a man, matters that the number of sperms, sperm activity, and whether sperms have deformity may be identified. Particularly, after improving the state of sperms, it is possible to try to get pregnant.

In analyzing semen, the subdivision pattern may be used as shown in FIGS. 10(a) and (b). By determining the number, activity, and the form of sperms positioned within the grid pattern formed in the middle of FIGS. 10(a) and (b), the sperm characteristic is easily analyzed. More specifically, all sperms distributed throughout the obtained image are not analyzed by the testing terminal 50 or a medical institution system (not shown), sampling analysis may be performed on targets that are sperms in the region delimited by the subdivision pattern. According to the present invention, quick analysis is possible, and pattern processing load of the testing terminal 50 may be reduced with more detailed analysis.

As an example of the subdivision pattern, although the grid form is shown in FIGS. 9 and 10, the pattern may be formed in various shapes, such as an oval, a circle, etc., and an arbitrary position may be specified as well as the center of the screen. Also, the image is checked, and the subdivision pattern is applied to the position with high density, whereby the analysis is conducted. The present invention is not limited thereto.

In order to analyze the sperm characteristic in the testing terminal 50 of the present invention, a similar method to the above-described saliva analysis is performed. First, the testing terminal 50 photographs the semen deposited on the sheet unit 20 and 120 to obtain the test image. The testing terminal 50 computes the number of sperms, travel distances of particular sperms, the average of the travel distances, whether to rotate, the rotation speed, and the rotation radius identified within a particular region in the test image. Here, the testing terminal 50 may obtain several test images for use, or may obtain the test image in the form of a video. Here, particular sperms in the image are randomly selected and the sperm characteristic of the randomly selected sperms is determined, whereby the state of sperms is identified. Also, the selection of multiple sperms for sampling may enhance accuracy of the analysis of the sperm characteristic.

Also, the testing terminal 50 selects some sperms in the test image, the image of the selected sperms is processed in a clear pattern or in a black-and-white image, and then the result is compared with a pre-stored image or with a predetermined condition whether to have a shape corresponding thereto, whereby whether sperm is malformed is determined. For example, whether sperms in the test image have a normal form may be identified by determining the number of end portions (tail shape) per head (round part), whether the end portion is bent, and malformation of the head.

Particularly, in this process, in order to facilitate selection and sampling of sperms, the subdivision pattern is applied as shown in FIG. 10, and the sperm characteristic may be analyzed by targeting the sperms positioned in the region defined by the subdivision pattern among sperms in the test image. Thus, selection of sperms for sampling may be easy, consistency of the analysis information may be maintained, and the load of the testing terminal 50 due to the analysis may be reduced, whereby quick analysis is possible.

Also, as shown in (c), the vaginal discharge is observed to determine the presence of disease symptoms, such as bacterial vaginosis, vaginitis, and whether to perform diagnosis. Specifically, when the vaginal discharge is observed by using an examination device, only vaginal mucosa cells are observed for a normal case. However, as shown in FIG. 10(c), when a disease caused by bacterial infection occurs, substances such as those shown as black spots in (c) are identified. (c) shows the case in which secretion of antibacterial substances inside the vagina decreased resulting in an increase of vaginal acidity and overgrowth of anaerobic bacteria. The overgrown anaerobic bacteria is adsorbed on the surface of the vaginal mucosa cell and the vaginal mucosa cells are covered with black spots, and the symptom is identified by the examination device. As a result, according to the present invention, body secretion such as the saliva, the vaginal discharge, and the semen of man is photographed in a magnified manner and an image analysis and a naked-eye analysis are conducted such that various states, such as the presence of the disease, the name of the disease, the ovulation period, are possibly determined.

While the exemplary embodiments of the invention have been described above, the embodiments are only examples of the invention, and it will be understood by those skilled in the art that the invention can be modified in various forms without departing from the technical spirit of the invention. Therefore, modifications of the present invention are appreciated as included in the scope and spirit of the invention, and the protection scope of the present invention will be defined by the accompanying claims.

INDUSTRIAL APPLICABILITY

The present invention is intended to propose a device available for both women and men, whereby a woman may identify the period of high pregnancy probability by checking her ovulation period and a man may identify his sperm viability, thereby using the device as a pregnancy auxiliary tool.

The invention claimed is:

1. A testing device for body fluid analysis, the device comprising:
    a sheet unit having a sheet of which a first surface receives body fluid of a user to be deposited thereon;
    a contact unit having a magnifying lens group for magnifying the body fluid deposited on the sheet, the contact unit being provided with a first side at which the magnifying lens group is placed to face the first surface of the sheet and being provided with a second side at which a guide adhering to a photographing means obtaining an image of the body fluid magnified by the magnifying lens group or coming into contact with around an eye of the user is placed; and
    a light source unit placed to face a second surface of the sheet of the sheet unit in a direction facing the contact unit with the sheet unit in between, the light source unit supplying external light to the second surface of the sheet,
    wherein the contact unit and the light source unit are formed in an integrated manner, and the sheet unit is fitted between the contact unit and the light source unit in such a manner as to be inserted and discharged,
    wherein the contact unit and the light source unit are formed with a hole or a slit in between for insertion of the sheet unit.

2. The device of claim 1, wherein the light source unit is formed in a shape of a hollow pipe.

3. The device of claim 2, wherein the light source unit is formed with a body hole as a light entering hole through which light enters.

4. The device of claim 1, wherein the light source unit includes a light transmissive film between a light entering hole through which light enters and the sheet unit.

5. The device of claim 4, wherein the film transmits only a predetermined wavelength of the external light such that the external light appears in a particular color.

6. The device of claim 1, wherein the sheet unit is provided with circumferential surfaces respectively formed on a side of the first surface and a side of the second surface, and
    the contact unit and the light source unit with the sheet unit in between are respectively coupled to the circumferential surfaces formed on the sides of the first and second surfaces of the sheet unit.

7. The device of claim 1, wherein the sheet is formed of any one material of light transmissive synthetic resin, natural rubber, and glass.

8. The device of claim 1, wherein the sheet is formed of a light transmissive material, the sheet being colored in a particular color or being formed of a material transmitting a particular light wavelength.

* * * * *